(12) United States Patent
Dahl et al.

(10) Patent No.: US 11,806,375 B2
(45) Date of Patent: *Nov. 7, 2023

(54) NUTRITIONAL SUPPORT FOR ANIMALS VIA ADMINISTRATION OF AN ALGAL DERIVED SUPPLEMENT

(71) Applicant: Zivo Bioscience, Inc., Keego Harbor, MI (US)

(72) Inventors: Andrew A. Dahl, Bloomfield Hills, MI (US); Amy E. Steffek, Royal Oak, MI (US)

(73) Assignee: Zivo Bioscience, Inc., Keego Harbor, MI (US)

(*) Notice: Subject to any disclaimer, the term of this patent is extended or adjusted under 35 U.S.C. 154(b) by 696 days.

This patent is subject to a terminal disclaimer.

(21) Appl. No.: 15/998,619

(22) PCT Filed: Feb. 15, 2017

(86) PCT No.: PCT/US2017/017906
§ 371 (c)(1),
(2) Date: Aug. 16, 2018

(87) PCT Pub. No.: WO2017/142906
PCT Pub. Date: Aug. 24, 2017

(65) Prior Publication Data
US 2020/0330535 A1    Oct. 22, 2020

Related U.S. Application Data

(60) Provisional application No. 62/457,566, filed on Feb. 10, 2017, provisional application No. 62/295,976, filed on Feb. 16, 2016.

(51) Int. Cl.
| | | |
|---|---|---|
| *A23L 17/60* | (2016.01) | |
| *A61K 36/05* | (2006.01) | |
| *A23K 50/10* | (2016.01) | |
| *A23K 10/30* | (2016.01) | |
| *A23L 33/105* | (2016.01) | |
| *A23L 33/00* | (2016.01) | |
| *A61K 9/00* | (2006.01) | |

(52) U.S. Cl.
CPC .............. *A61K 36/05* (2013.01); *A23K 10/30* (2016.05); *A23K 50/10* (2016.05); *A23L 17/60* (2016.08); *A23L 33/105* (2016.08); *A23L 33/40* (2016.08); *A61K 9/0019* (2013.01); *A61K 9/0095* (2013.01); *A23V 2002/00* (2013.01)

(58) Field of Classification Search
CPC .... A61K 36/05; A61K 9/0019; A61K 9/0095; A61K 36/02; A23K 50/10; A23K 10/30; A23L 17/60; A23L 33/105; A23L 33/40; A23V 2002/00
See application file for complete search history.

(56) References Cited

U.S. PATENT DOCUMENTS

| | | | |
|---|---|---|---|
| 4,012,504 A | 3/1977 | Eckols | |
| 4,303,409 A | 12/1981 | Ogawa et al. | |
| 4,439,196 A | 3/1984 | Higuchi | |
| 4,447,224 A | 5/1984 | DeCant et al. | |
| 4,447,233 A | 5/1984 | Mayfield | |
| 4,471,055 A | 9/1984 | Opp | |
| 4,475,196 A | 10/1984 | La Zor | |
| 4,486,194 A | 12/1984 | Ferrara | |
| 4,487,603 A | 12/1984 | Harris | |
| 4,822,612 A | 4/1989 | Shinpo | |
| 4,915,965 A * | 4/1990 | Tanaka | A23L 17/60 426/138 |
| 4,925,678 A | 5/1990 | Ranney | |
| 4,959,217 A | 9/1990 | Sanders | |
| 5,167,616 A | 12/1992 | Haak et al. | |
| 5,169,383 A | 12/1992 | Gyory et al. | |
| 5,225,182 A | 7/1993 | Sharma | |

(Continued)

FOREIGN PATENT DOCUMENTS

| | | |
|---|---|---|
| CA | 2564466 | 12/2005 |
| CA | 2485449 | 4/2006 |

(Continued)

OTHER PUBLICATIONS

Amaro, H. et al., "Antimicrobial activities of microalgae: an invited review." Science against microbial pathogens: communicating current research and technological advances (Ed. Mendez-Vilas, A.), Formatex Research Center, Spain, 2011, ISBN-13: 978-84-939843-1-1, pp. 1272-1280.*
Amaro, H. et al. Antimicrobial activities of microalgae: An invited review, 2011, 1272-1280 (Year: 2011).*
Causes and Prevention of Coccidiosis in your Flock, 2011, https://hcsummers.com/blog/3488/causes-and-prevention-of-coccidiosis-in-your-flock (Year: 2011).*
Brooks, K. Three Billion Year-Old Solution to Stress, Anxiety and Depression, 2010, Nutri Centre, https://www.healthy.co.uk/blog/klamath-algae-stress-anxiety-depression (Year: 2010).*
Bagley, C. Bovine Respiratory Disease, 1997, Utah State University Cooperative Extension, 1-4 (Year: 1997).*

(Continued)

*Primary Examiner* — Louise W Humphrey
*Assistant Examiner* — Anjali Ajit Hirani
(74) *Attorney, Agent, or Firm* — Snell & Wilmer L.L.P.

(57) ABSTRACT

An algal biomass and supernatant derived from at least one species of algae exhibits the ability to maintain general health in humans and non-human animals and promote a healthy immune system in them. Food, feed and nutritional supplements comprising an algal biomass or supernatant derived from at least one species of algae are described. Methods of maintaining general health or promoting a healthy immune system in humans and non-human animals comprises administering to the animal in need thereof an algal biomass or supernatant derived from at least one species of algae, or an extract, derivative or homeopathic compound derived from the algae species, biomass or supernatant, or a composition thereof.

2 Claims, No Drawings

(56) References Cited

U.S. PATENT DOCUMENTS

| | | | |
|---|---|---|---|
| 5,726,063 | A | 3/1998 | Gerard-Monnier et al. |
| 5,767,095 | A | 6/1998 | Winget |
| 6,235,495 | B1 | 5/2001 | Fu et al. |
| 6,374,874 | B1 | 4/2002 | Payne |
| 6,461,607 | B1 | 10/2002 | Farmer |
| 6,551,596 | B2 | 4/2003 | Kralovec |
| 6,673,908 | B1 | 1/2004 | Stanton |
| 6,733,751 | B2 | 5/2004 | Farmer |
| 7,025,965 | B1 | 4/2006 | Pieloch |
| 7,125,846 | B2 | 10/2006 | Rojkjaer |
| 7,807,622 | B2 | 10/2010 | Thomas et al. |
| 8,586,053 | B2 | 11/2013 | Thomas et al. |
| 8,791,060 | B2 | 7/2014 | Thomas et al. |
| 9,486,005 | B2 | 11/2016 | Gupta et al. |
| 10,166,270 | B2 | 1/2019 | Thomas et al. |
| 10,232,028 | B2 | 3/2019 | Dahl |
| 2002/0009479 | A1 | 1/2002 | Vardi et al. |
| 2002/0119164 | A1 | 8/2002 | Uchiyama et al. |
| 2003/0015587 | A1 | 8/2003 | Kralovec |
| 2003/0152587 | A1 | 8/2003 | Kralovec |
| 2005/0114920 | A1 | 5/2005 | Yusibov et al. |
| 2005/0229585 | A1 | 10/2005 | Webster |
| 2005/0260695 | A1 | 11/2005 | Flemming et al. |
| 2006/0101803 | A1 | 5/2006 | White |
| 2007/0010480 | A1 | 1/2007 | Rusing et al. |
| 2007/0207231 | A1 | 9/2007 | Thomas et al. |
| 2008/0031863 | A1 | 2/2008 | Hildreth et al. |
| 2008/0089843 | A1 | 4/2008 | Pillarisetti et al. |
| 2008/0119571 | A1 | 5/2008 | Khanna et al. |
| 2008/0272232 | A1 | 11/2008 | Cagle et al. |
| 2008/0272615 | A1 | 11/2008 | Mcknight et al. |
| 2009/0036372 | A1 | 2/2009 | Thomas et al. |
| 2009/0117216 | A9 | 5/2009 | Thomas et al. |
| 2010/0028488 | A1 | 2/2010 | Lo et al. |
| 2011/0081319 | A1 | 4/2011 | Thomas et al. |
| 2011/0117122 | A1 | 5/2011 | Thomas et al. |
| 2011/0124544 | A1 | 5/2011 | He et al. |
| 2011/0143012 | A1* | 6/2011 | Rettenmaier ........... B01D 53/84 426/648 |
| 2011/0307976 | A1 | 12/2011 | Ploechinger |
| 2012/0328598 | A1 | 12/2012 | Gupta et al. |
| 2013/0251698 | A1 | 9/2013 | Thomas et al. |
| 2015/0157688 | A1 | 6/2015 | Thomas et al. |
| 2015/0201649 | A1* | 7/2015 | Lei ...................... A23K 20/142 424/602 |
| 2016/0120970 | A1 | 5/2016 | Dahl et al. |
| 2017/0135391 | A1 | 5/2017 | Gupta et al. |
| 2017/0360883 | A9 | 12/2017 | Thomas et al. |
| 2018/0021392 | A1 | 1/2018 | Dahl et al. |
| 2018/0255820 | A1 | 9/2018 | Dahl |

FOREIGN PATENT DOCUMENTS

| | | |
|---|---|---|
| CA | 2827401 | 8/2011 |
| CN | 102225127 | 10/2011 |
| EP | 1230927 | 8/2002 |
| EP | 1878877 | 1/2008 |
| EP | 1928247 | 10/2009 |
| EP | 2501390 | 9/2012 |
| EP | 2538951 | 1/2013 |
| EP | 3416501 | 12/2018 |
| HK | 1248545 | 10/2018 |
| JP | 0940523 | 2/1997 |
| JP | 2009518312 | 5/2009 |
| JP | 2014006051 | 1/2014 |
| WO | 2011060427 | 5/2001 |
| WO | 2003028749 | 4/2003 |
| WO | 2005112987 | 1/2005 |
| WO | 2006055217 | 5/2006 |
| WO | 2006113925 | 10/2006 |
| WO | 2007065024 | 6/2007 |
| WO | WO-2010042842 A2 * | 4/2010 ............... C12P 7/649 |
| WO | 2011016973 | 2/2011 |
| WO | 2011103569 | 8/2011 |
| WO | 2014201372 | 12/2014 |
| WO | 2016133922 | 8/2016 |
| WO | 2017142906 | 8/2017 |
| WO | 2018165205 | 9/2018 |

OTHER PUBLICATIONS

Ionescu, N. et al., Fatty Acids and Antioxidant Activity in Vegetable Oils Used in Cosmetic Formulations, 2015, UPB Scientific Bulletin, Series B, 77(3): 39-48 (Year: 2015).*

Energybits Recoverybits, 2014, https://web.archive.org/web/20140323102555/https://www.energybits.com/recoverybits.html (Year: 2014).*

USPTO; Final Office Action dated Apr. 10, 2019 in U.S. Appl. No. 15/550,749.

USPTO; Non-Final Office Action dated Apr. 19, 2019 in U.S. Appl. No. 15/330,830.

USPTO; Non-Final Office Action dated Mar. 11, 2019 in U.S. Appl. No. 16/273,794.

EPO; Examination Report dated Feb. 22, 2019 in Application No. EP11745434.

Solomon et al., "Midlife Serum Cholesterol and Increased Risk of Alzheimer's and Vascular Dementia Three Decades Later," Dementia and Geriatric Cognitive Disorders, vol. 28(1), pp. 75-80, (Aug. 2009).

Li et al., "Inactivation of Nuclear Factor kB by Soy Isoflavone Genistein Contributes to Increased Apoptosis Induced by Chemotherapeutic Agents in Human Cancer Cells," Cancer Research, vol. 65(15), pp. 6934-6942, (2005).

USPTO; Non-Final Office Action dated Sep. 17, 2018 in U.S. Appl. No. 15/550,749.

USPTO; Notice of Allowance dated Oct. 29, 2018 in U.S. Appl. No. 14/898,091.

EPO; Supplementary Search Report dated Aug. 28, 2018 in EP16752918.9.

EPO; Extended Search Report dated Aug. 10, 2018 in EP16752918.9.

PCT; International Preliminary Report on Patentability dated Aug. 21, 2018 in PCT/US2017/017906.

PCT; International Search Report dated Jun. 28, 2018 in International Application No. PCT/2018/021215.

PCT; Written Opinion dated Jun. 28, 2018 in International Application No. PCT/US2018/021215.

FDA, "Data Standards Manual: Route of Administration," www.fda.gov/Drugs/DevelopmentApprovalProcess/FormsSubmissionRequirements.gov, (Revised Jan. 11, 2006).

USPTO; Advisory Action dated Mar. 6, 2009 in U.S. Appl. No. 11/606,676.

USPTO; Final Office Action dated May 29, 2009 in U.S. Appl. No. 11/606,676.

USPTO; Final Office Action dated Nov. 14, 2008 in U.S. Appl. No. 11/606,676.

USPTO; Office Action dated Feb. 4, 2008 in U.S. Appl. No. 11/606,676.

USPTO; Office Action dated Oct. 8, 2009 in U.S. Appl. No. 11/606,676.

USPTO; Notice of Allowance dated May 27, 2010 in U.S. Appl. No. 11/606,676.

USPTO; Examiner Interview Summary Record dated Apr. 12, 2010 in U.S. Appl. No. 11/606,676.

USPTO; Final Office Action dated Nov. 3, 2008 in U.S. Appl. No. 11/587,266.

USPTO; Non-Final Office Action dated Feb. 4, 2008 in U.S. Appl. No. 11/587,266.

USPTO; Office action dated Oct. 22, 2012 in U.S. Appl. No. 12/067,735.

USPTO; Requirement for Restriction dated Oct. 19, 2010 in U.S. Appl. No. 12/067,735.

USPTO; Requirement for Restriction dated Jul. 20, 2011 in U.S. Appl. No. 12/067,735.

USPTO; Office Action dated Mar. 13, 2012 in U.S. Appl. No. 12/067,735.

(56) References Cited

OTHER PUBLICATIONS

USPTO; Final Office Action dated Oct. 23, 2012 in U.S. Appl. No. 12/067,735.
USPTO; Notice of Allowance dated May 13, 2013 in U.S. Appl. No. 12/067,735.
USPTO; Notice of Allowance dated Aug. 15, 2013 in U.S. Appl. No. 12/067,735.
USPTO; Advisory Action dated Feb. 26, 2014 in U.S. Appl. No. 12/897,574.
USPTO; Non-Final Office Action dated Jun. 24, 2013 in U.S. Appl. No. 12/897,574.
USPTO; Final Office Action dated Nov. 13, 2013 in U.S. Appl. No. 12/897,574.
USPTO; Notice of Allowance dated Apr. 8, 2014 in U.S. Appl. No. 12/897,574.
USPTO; Final Office Action dated May 21, 2012 in U.S. Appl. No. 12/947,684.
USPTO; Final Office Action dated Oct. 9, 2013 in U.S. Appl. No. 12/947,684.
USPTO; Office Action dated Sep. 9, 2011 in U.S. Appl. No. 12/947,684.
USPTO; Office Action dated Dec. 20, 2012 in U.S. Appl. No. 12/947,684.
USPTO; Advisory Action dated Aug. 7, 2015 in U.S. Appl. No. 13/580,471.
USPTO; Final Office Action dated Apr. 2, 2015 in U.S. Appl. No. 13/580,471.
USPTO; Office Action dated Aug. 26, 2014 in U.S. Appl. No. 13/580,471.
USPTO; Notice of Allowance dated Jun. 20, 2016 in U.S. Appl. No. 13/580,471.
USPTO; Restriction Requirement dated Mar. 4, 2014 in U.S. Appl. No. 13/580,471.
USPTO; Office Action dated Dec. 8, 2015 in U.S. Appl. No. 13/580,471.
USPTO; Office Action dated Jun. 2, 2014 in U.S. Appl. No. 13/841,739.
USPTO; Office Action dated Jun. 1, 2017 in U.S. Appl. No. 14/558,516.
USPTO; Notice of Allowance dated Jan. 12, 2018 in U.S. Appl. No. 14/558,516.
USPTO; Restriction Requirement dated Dec. 23, 2016 in U.S. Appl. No. 14/558,516.
USPTO; Final Office Action dated May 1, 2017 in U.S. Appl. No. 14/898,091.
USPTO; Office Action dated Jun. 28, 2016 in U.S. Appl. No. 14/898,091.
USPTO; Office Action dated Oct. 3, 2016 in U.S. Appl. No. 14/898,091.
USPTO; Final Office Action dated Jun. 5, 2018 in U.S. Appl. No. 14/898,091.
USPTO; Restriction Requirement dated Dec. 18, 2012 in U.S. Appl. No. 13/397,360.
USPTO; Office Action dated Jun. 19, 2014 in U.S. Appl. No. 13/397,360.
USPTO; Restriction Requirement dated Apr. 20, 2018 in U.S. Appl. No. 15/550,749.
USPTO; Restriction Requirement dated Aug. 6, 2018 in U.S. Appl. No. 15/330,830.
USPTO; Notice of Allowance dated Aug. 27, 2018 in U.S. Appl. No. 14/558,516.
Australia: Examination Report dated Aug. 30, 2011 in AU2006320264.
Australia: Examination Report dated Sep. 7, 2012 in AU2006320264.
Australia: Examination Report dated Apr. 11, 2014 in AU2013204257.
Canadian: Examination Report dated Feb. 26, 2015 in CA2631773.
Canadian: Examination Report dated Mar. 31, 2016 in CA2631773.
Canadian: Examination Report dated Apr. 2, 2014 in CA2631773.
Canadian: Examination Report dated May 24, 2013 in CA2631773.
Canadian: Examination Report dated May 16, 2017 in CA2631773.
Canadian; Examination Report dated Jun. 27, 2018 in CA2631773.
Canadian: Examination Report dated Mar. 28, 2017 in CA2780144.
Canadian: Examination Report dated Aug. 15, 2016 in CA2780144.
Canadian; Examination Report dated Mar. 29, 2018 in CA2827401 (8/29).
EPO: Extended Search Report/Written Opinion dated Nov. 2, 2017 in EP20111745434.
EPO: Examination Report dated Mar. 22, 2012 in EP2006320264.
EPO: Examination Report dated Oct. 13, 2009 in EP2006320264.
EPO: Supplemental Search Report—Written Opinion dated Sep. 24, 2009 in EP2006758513.
EPO; Examination Report dated Nov. 20, 2009 in EP2006758513.
EPO; Examination Report dated Mar. 22, 2012 in EP2006758513.
EPO: Examination Report dated Mar. 31, 2016 in EP2010830908.
EPO: Extended Search Report dated Jun. 2, 2014 in EP2010830908.
EPO: Office Action dated Feb. 23, 2010 in EP2006838974.
Japan: Examination Report dated Aug. 7, 2012 in JP200854345.
Japan: Examination Report dated Nov. 11, 2014 in JP2012539974.
PCT: International Search Report and Written Opinion dated Jul. 29, 2011 in International Application No. PCT/US2010/056862.
PCT: International Preliminary Report on Patentability dated May 22, 2012 in International Application No. PCT/US2010/056862.
PCT: Written Opinion dated Sep. 24, 2014 in International Application No. PCT/US2014/042331.
PCT: International Search Report dated Sep. 24, 2014 in International Application No. PCT/US2014/042331.
PCT: International Preliminary Report on Patentability dated Dec. 15, 2015 in International Application No. PCT/US2014/042331.
PCT: Written Opinion dated May 25, 2017 in International Application No. PCT/US2017/017906.
PCT: International Search Report dated May 25, 2017 in International Application No. PCT/US2017/017906.
PCT: Written Opinion dated Aug. 4, 2016 in International Application No. PCT/US2016/018105.
PCT: International Search Report dated Aug. 4, 2016 in International Application No. PCT/US2016/018105.
PCT: International Preliminary Report on Patentability dated Aug. 22, 2017 in International Application No. PCT/US2016/018105.
PCT: Written Opinion dated Jun. 21, 2011 in International Application No. PCT/US2011/025713.
PCT: International Search Report dated Jun. 21, 2011 in International Application No. PCT/US2011/025713.
PCT: International Preliminary Report on Patentability dated Aug. 28, 2012 in International Application No. PCT/US2011/025713.
PCT: Written Opinion dated Dec. 6, 2005 in International Application No. PCT/US2005/013375.
PCT: International Preliminary Report on Patentability dated Oct. 25, 2006 in International Application No. PCT/US2005/013375.
PCT: Written Opinion dated Mar. 22, 2007 in International Application No. PCT/US2006/015302.
PCT: International Preliminary Report on Patentability dated Oct. 23, 2007 in International Application No. PCT/US2006/015302.
PCT: International Search Report dated Oct. 17, 2007 in International Application No. PCT/US2006/046320.
PCT: International Search Report dated Feb. 23, 2012 in International Application No. PCT/US2011/44786.
PCT: Written Opinion dated Feb. 23, 2012 in International Application No. PCT/US2011/44786.
PCT: International Preliminary Report on Patentability dated Jan. 29, 2013 in International Application No. PCT/US2011/44786.
Amaro et al., "Antimicrobial Activities of Microalgae: An Invited Review," Science Against Microbial Pathogens: Communicating Current Research and Technological Advances (Ed. Mendez-Vilas, A.), Formatex Research Center, Spain, ISBN-13: 978-84-939843-1-1, pp. 1272-1280, (2011).
Bhadury et al., "Exploitation of Marine Algae: Biogenic Compounds for Potential Antifouling Applications," Planta, (E-pub), vol. 219, No. 4, pp. 561-578, (Jun. 24, 2004).
Brewer et al., "Arteriosclerosis, Thrombosis, and Vascular Biology: Regulation of Plasma High-Density Lipoprotein Levels by the ABCA1 Transporter and the Emerging Role of High-Density Lipoprotein in the Treatment of Cardiovascular Disease," American Heart Association, vol. 24(24), pp. 1755-1760, (Aug. 19, 2004).

(56) References Cited

OTHER PUBLICATIONS

Fujita, "NF-KB: Regulation and Genetic Engineering of Signal Transduction of Inflammation," Journal of Clinical and Experimental Medicine, vol. 190(10), pp. 913-916, (1999).

Kim et al., "Purification and Characterization of a Fibrinolytic Enzyme Produced from *Bacillus* sp.strain CK 11-4 Screened from Chungkook-Jang," Environ. Microbiology, vol. 62, No. 7, pp. 2482-2488, (Jul. 1996).

Kim, Young-Gon, and Moon-Seog Jun, "A Design of User Authentication System Using QR Code Identifying Method," Computer Sciences and Convergence Information Technology (ICCIT), 6th International Conference on IEEE, (Nov. 29-Dec. 1, 2011).

Mudimu et al., "Biotechnological Screening of Microalgal and Cyanobacterial Strains for Biogas Production and Antibacterial and Antifungal Effects," Metabolites, vol. 4, No. 2, pp. 373-393, (May 15, 2014).

Noda et al., "A Water-Soluble Antitumor Glycoprotein from Chlorella Vulgaris," Faculty of Pharmaceutical Sciences, Kyushu University, (Oct. 1996) Abstract Only.

Oben et al., "The Effects of ProAlgaZyme Novel Algae Infusions on Metabolic Syndrome and Markers of Cardiovascular Health," Lipids in Health and Disease, vol. 6, pp. 1-9, (2007).

Oben et al., "Lipids in Health and Disease: The Effects of ProAlgaZyme Novel Algae Infusion of Metabolic Syndrome and Markers of Cardiovascular Health," BioMed Central, pp. 1-9, (Sep. 5, 2007).

Okada et al., "Inflammatory Bowel Disease and Cytokine," Journal of Clinical and Experimental Medicine, pp. 265-268, (Oct. 2004).

Press Release entitled, "Western Glory Hole Inc. Enters Definitive Agreement with Health Enhancement Products In," Business Wire, (Oct. 30, 2003).

Sarkar et al., "Using Chemopreventive Agents to Enhance the Efficacy of Cancer Therapy," Cancer Research, vol. 66(7), pp. 3347-3350, (Apr. 1, 2006).

"BioSuperfood—Algae/Spirulina for People," Optimum Choices, pp. 1-23, http://www.optimumchoices.com/spirulina.htm., (Apr. 14, 2010).

"Spirulina," MedlinePlus, U.S. National Library of Medicine and the National Institutes of Health, http://www.nlm.nih.gov/medlineplus/druginfo/natural/patient-spirulina.html., (Apr. 14, 2010).

Gupta et al., "ProAlgaZyme and its Sub-Fractions Increase Plasma HDL-Cholesterol Via Up Regulation of ApoA1, ABCA1 and SRB1 and Inhibition of CETP in Hypercholesterolemic Hamsters," Journal of Nutrition and Food Science, WSU, (Jun. 2012).

www.michaelkiriac.com, (Jan. 1, 2003).

"Research Indicates ProAlgaZyme May Decrease Risk of Stroke or Heart Attack," Supplemental Quality.com, pp. 10, 11, (Jan. 20, 2004).

\* cited by examiner

NUTRITIONAL SUPPORT FOR ANIMALS VIA ADMINISTRATION OF AN ALGAL DERIVED SUPPLEMENT

CROSS-REFERENCE TO RELATED APPLICATIONS

This application is a U.S. National Phase filing under 35 U.S.C. § 371 of PCT Application Ser. No. PCT/US2017/017906 filed on Feb. 15, 2017, which claims priority to U.S. Provisional Patent Application Ser. No. 62/295,976, filed Feb. 16, 2016, entitled "Nutritional Support for Animals via Administration of an Algal Derived Supplement," and U.S. Provisional Patent Application Ser. No. 62/457,566, filed Feb. 10, 2017, entitled "Nutritional Support for Humans via Administration of an Algal Derived Supplement," the contents of which are incorporated herein by reference in their entireties.

FIELD OF THE INVENTION

The present invention relates to nutritional support in human and non-human animals, and in particular to a composition comprising algal derived materials capable of supporting a healthy immune system in an animal and methods of treatment thereof.

BACKGROUND OF THE INVENTION

People from all over the globe now turn to nutritional supplements, nutraceuticals and homeopathic preparations for their general health and wellbeing. The global vitamin and supplements market is now valued at close to $100 billion and is expected to keep increasing. It has been recognized for years that nutritional supplements are needed because many people do not have healthy diets to fulfill their dietary needs. Furthermore, it is known that some nutrients help support a healthy immune system, such as vitamin C, beta-carotene and vitamin E. Many supplements, nutraceuticals and homeopathic preparations are marketed today as promoting a healthy immune system, increasing bone health, increasing muscle tone, lowering stress, coping with stress, and lowering the risk of contracting diseases.

In humans, it is well established that insufficient nutrition, and even physical and emotional stress, lowers a person's immunity to infections and chronic diseases. Current research supports the notion that good nutrition can prevent many disease states, and can reduce the recovery time during medical treatment of various diseases, injury or other stress and immune related injuries and illnesses. It is now known, for example, that calcium and vitamin D are important in human nutrition for bone strength and to prevent bone loss, folic acid decreases the risk of certain birth defects, and omega-3 fatty acids (e.g. fish oils) may reduce the incidence of heart disease.

Non-human animals also have nutritional needs that are unmet by animal feed alone. Furthermore, animals such as cattle and fowl can be stressed, which lowers the animals' immunity to infections and chronic diseases. Stress in animals also reduces animal weight and reduces the quality and quantity of egg and milk production. Some stress in animals is natural and unavoidable, such as birthing. Nutritional support has become important for improving outcomes in animals under stress. Discoveries about nutritional therapy substantiate the importance of providing nutritional support to animals even under the watchful care of veterinarians. Current research supports the notion that good nutrition can prevent many disease states and can reduce the recovery time during the medical treatment of various diseases, injury or other stress and immune related injuries and illnesses. It is now known that specific nutrients can be used to reduce the effects of stress in animals, including for example, dehydration, loss of energy, an imbalance of symbiotic bacteria, low body weight, low milk production, low egg production, inferior milk, inferior eggs, gastrointestinal disorders, and general issues relating to a weakened immune system.

In view of the continuing health needs of animals and humans all over the world, new nutritional compositions, supplements, animal foods and feeds, medicaments, nutraceuticals, and homeopathic preparations are always needed that can promote a healthy immune system and promote general health.

SUMMARY OF THE INVENTION

A nutritional composition for humans and non-human animals is disclosed and comprises an algal biomass or supernatant derived from at least one species of algae. An exemplary algal biomass and supernatant may be obtained by processing the biological material of NCMA Deposit #PATENT201602001. In certain aspects, the biological material of NCMA Deposit #PATENT201602001 includes a *klebsormidium* species of algae.

An algal biomass and a supernatant, derived from at least one species of algae, promote a healthy immune system and promote general health in a human or a non-human animal. An exemplary algal biomass and supernatant may be obtained by processing the biological material of NCMA Deposit #PATENT201602001. In certain aspects, the biological material of NCMA Deposit #PATENT201602001 includes a *klebsormidium* species of algae.

The disclosure further provides a composition comprising an algal biomass and/or a supernatant derived from at least one species of algae, wherein the composition promotes a healthy immune system and promotes general health in a human or non-human animal. In exemplary aspects, an algal biomass and supernatant may be obtained by processing the biological material of NCMA Deposit #PATENT201602001. In certain aspects, the biological material of NCMA Deposit #PATENT201602001 includes a *klebsormidium* species of algae.

A method of producing an algal biomass and a supernatant, each usable in promoting a healthy immune system and general health in a human or non-human animal, comprises obtaining a sample of the biological material of NCMA Deposit #PATENT201602001 and separating the cellular matter from the liquid present. In certain aspects, the biological material of NCMA Deposit #PATENT201602001 includes a *klebsormidium* species of algae.

The disclosure further provides human nutritional supplement compositions, and methods for compounding supplements, wherein a supplement comprises an algal biomass or supernatant derived from at least one species of algae, or wherein a supplement comprise an extract, derivative, or homeopathic compound derived from an algal biomass or supernatant further derived from at least one species of algae. In exemplary aspects, an algal biomass and supernatant may be obtained by processing the biological material of NCMA Deposit #PATENT201602001. In certain aspects, the biological material of NCMA Deposit #PATENT201602001 includes a *klebsormidium* species of algae.

The present disclosure provides methods for promoting or supporting a healthy immune system and/or promoting general health in an animal, human or non-human, by administering to the animal in need thereof, a prophylactically effective amount of an algal biomass or supernatant derived from at least one species of algae. In certain examples, the at least one species of algae comprises a *klebsormidium* species of algae. In certain aspects, the biological material of NCMA Deposit #PATENT201602001 includes a *klebsormidium* species of algae.

A method for promoting or supporting a healthy immune system in a human or non-human animal comprises administering to the animal in need thereof a prophylactically effective amount of a composition or supplement comprising an algal biomass or supernatant derived from at least one species of algae. In various embodiments, the animal in need of treatment thereof is a beef or dairy cow, a dog, a cat, a horse, a goat, a pig, any other livestock, or a human. In certain examples, the at least one species of algae comprises a *klebsormidium* species of algae. In certain aspects, the biological material of NCMA Deposit #PATENT201602001 includes a *klebsormidium* species of algae.

A method of promoting the general health of a human or non-human animal comprises administering to the animal in need thereof a prophylactically effective amount of an algal biomass or supernatant derived from at least one species of algae. In various embodiments, the animal in need of treatment thereof is a beef or dairy cow, a dog, a cat, a horse, a goat, a pig, any other livestock, or a human. In certain examples, the at least one species of algae comprises a *klebsormidium* species of algae. In certain aspects, the biological material of NCMA Deposit #PATENT201602001 includes a *klebsormidium* species of algae.

A method of promoting general health in a human or non-human animal comprises administering to the animal in need thereof a prophylactically effective amount of a composition or supplement comprising an algal biomass or supernatant derived from at least one species of algae. In various embodiments, the animal in need of treatment thereof is a beef or dairy cow, a dog, a cat, a horse, a goat, a pig, any other livestock, or a human. In certain examples, the at least one species of algae comprises a *klebsormidium* species of algae. In certain aspects, the biological material of NCMA Deposit #PATENT201602001 includes a *klebsormidium* species of algae.

A method of reducing or preventing recurrence of a disease in a human or non-human animal comprises administering to the animal in need thereof a prophylactically effective amount of an algal biomass or supernatant derived from at least one species of algae. In various embodiments, the animal in need of treatment thereof is a beef or dairy cow, a dog, a cat, a horse, a goat, a pig, any other livestock, or a human. In certain examples, the at least one species of algae comprises a *klebsormidium* species of algae. In certain aspects, the biological material of NCMA Deposit #PATENT201602001 includes a *klebsormidium* species of algae.

A method of reducing or preventing recurrence of a disease in a human or non-human animal comprises administering to the animal in need thereof a prophylactically effective amount of a composition or supplement comprising an algal biomass or supernatant derived from at least one species of algae. In various embodiments, the animal in need of treatment thereof is a beef or dairy cow, a dog, a cat, a horse, a goat, a pig, any other livestock, or a human. In certain examples, the at least one species of algae comprises a *klebsormidium* species of algae. In certain aspects, the biological material of NCMA Deposit #PATENT201602001 includes a *klebsormidium* species of algae.

A method of reducing or preventing the effects of everyday stress or event-related stress in a human and for reducing or preventing the effects of stress in a non-human animal comprises administering to the animal in need thereof a prophylactically effective amount of an algal biomass or supernatant derived from at least one species of algae. In various embodiments, the animal in need of treatment thereof is a beef or dairy cow, a dog, a cat, a horse, a goat, a pig, any other livestock, or a human. In certain examples, the at least one species of algae comprises a *klebsormidium* species of algae. In certain aspects, the biological material of NCMA Deposit #PATENT201602001 includes a *klebsormidium* species of algae.

A method of reducing or preventing the effects of everyday stress or event-related stress in a human and for reducing or preventing the effects of stress in an animal comprises administering to the animal in need thereof a prophylactically effective amount of a composition or supplement comprising an algal biomass or supernatant derived from at least one species of algae. In various embodiments, the animal in need of treatment thereof is a beef or dairy cow, a dog, a cat, a horse, a goat, a pig, any other livestock, or a human. In certain examples, the at least one species of algae comprises a *klebsormidium* species of algae. In certain aspects, the biological material of NCMA Deposit #PATENT201602001 includes a *klebsormidium* species of algae.

DETAILED DESCRIPTION OF THE INVENTION

An algal biomass or supernatant, derived from a single algal species or multiple algae species, promotes general health in animals, promotes a healthy immune system in animals, prevents or reduces the recurrence of a disease in an animal and prevents or reduces the effects of stress in an animal. Further, an algal biomass or supernatant, derived from a single algal species or multiple algae species, reduces the effects of everyday stress and event-related stress in a human. In various embodiments, methods of promoting general health in animals, promoting a healthy immune system in animals, preventing or reducing the recurrence of a disease in an animal, preventing or reducing the effects of stress in a non-human animal, and reducing the effects of everyday stress and event-related stress in a human comprises administering to the animal in need thereof a prophylactically effective amount of an algal biomass or supernatant derived from at least one species of algae. Also, a method comprises administering to an animal in need thereof a prophylactically effective amount of a composition or supplement comprising an algal biomass or supernatant derived from at least one species of algae. Furthermore, a method comprises administering a prophylactically effective amount of an extract, derivative or homeopathic compound derived from at least one species of algae, or derived from an algal biomass or supernatant further derived from at least one species of algae, to an animal in need thereof. In various embodiments, the animal in need thereof is a beef or dairy cow, a dog, a cat, a horse, a goat, a pig, any other livestock, or a human. In other aspects of the invention, the animal in need thereof is a beef or dairy cow, or a dog, or human. In various embodiments, the at least one species of algae comprises a *klebsormidium* species of algae. The at least one species of algae may be part of the biological material of NCMA Deposit #PATENT201602001.

The term "animal" is used herein to refer to all animals, human or otherwise. In some instances, the term "non-human animal" may be used to distinguish from human animals. Otherwise, the term "animal" should be construed to mean all animals of any kind. In various embodiments, the term "animal" may refer to, for example, a beef or dairy cow, a dog, a cat, a bird, a fish, a horse, a goat, a sheep, a pig, various other livestock animals, or a human. In various embodiments, the term "animal" refers to common agricultural livestock animals such as bovine, porcine, and poultry, and the like. In certain aspects, the term "animal" may refer to more exotic or non-domesticated animals such as camels, primates and zoo animals in general.

As used herein, the term "supplement" is meant to broadly encompass all physical forms of a nutritional product intended for humans, which encompass any mode of administration to a human in need of any type and level of nutritional support. Thus, a "supplement" herein can be the "dosage form" or the "unit dose" of a nutritional composition, similar to a dosage form of a pharmaceutical drug product. In certain aspects, a composition may be the starting material for a supplement (e.g. in the way a bulk powder composition may be tableted into supplements in the form of tablets). A supplement in accordance to the present disclosure may be designed for oral or sublingual administration to a human, and thus may be in the form of a pill, tablet, caplet, soft capsule, powder filled capsule, chewable wafer or nodule, thin film/dissolving strip, liquid, or syrup. Supplements designed for nasal administration to a human, for example, may be in the form of a liquid composition, such as packaged as a nasal spray. Other supplements for human consumption may be in the form of transdermal creams, transdermal patches, suppositories, injectable liquids, aerosols for inhalation, or any other preparations capable of self-administration or administration by a health care professional to provide nutritional support to a human.

As used herein, the term "consumption" broadly means "usage" by a human or a non-human animal and is not limited to just oral consumption of a nutritional supplement (e.g. eating an animal feed or swallowing a pill) since the term "consumption" extends to, for example, usage of a product by injection, inhalation, or transdermal penetration.

Algal biomass and Supernatant from Algae; and Extracts, Derivatives and Biologically Active Compounds Derived from Algae and/or from an Algal Biomass:

The term "algal biomass" is used herein to generally refer to cellular material (e.g. whole algal cells) derived from naturally occurring or genetically modified algae ("GMO algae"). For example, in various embodiments, an algal biomass comprises freeze-dried or otherwise desiccated algae of one or more species of algae. In various embodiments, an algal biomass may comprise powdered or granulated desiccated algae from one or more species. An exemplary algal biomass may be derived from a *klebsormidium* species of algae by freeze-drying the cellular material and optionally powdering, milling or otherwise granulating the cellular material obtained upon drying. In certain aspects, an algal biomass is obtained by processing the biological material of NCMA Deposit #PATENT201602001, such as, for example, by draining and/or compressing it to remove liquid components (the "supernatant") and then freeze-drying the remaining cellular material. In various embodiments, the biological material of NCMA Deposit #PATENT201602001 comprises at least one *klebsormidium* species of algae.

An algal biomass may comprise whole algal cells of one or more algal cultures grown in distilled or conditioned water supplemented with various sterilized nutritive materials. A deposit of biological material that can be used to obtain an algal biomass and supernatant in accordance to the present disclosure was originally deposited on Oct. 6, 2006 at the Provasoli-Guillard National Center for Marine Algae and Microbiota— Bigelow Laboratory for Ocean Sciences, (NCMA), 60 Bigelow Drive, East Boothbay, Me. 04544, U.S.A., and assigned by the International Depositary Authority accession # PATENT201602001. This deposit is available to the public upon grant of a patent disclosing the same. This deposit was made pursuant to 37 C.F.R. § 1.808 and MPEP § 2410.01 and, therefore, access to the deposit will be available during pendency of this application making reference to the deposit to one determined by the Commissioner to be entitled thereto under 37 C.F.R. § 1.14 and 35 U.S.C. § 122 and with one exception, that all restrictions imposed by the depositor on the availability of the deposited biological material to the public be irrevocably removed upon the granting of the patent.

A method of producing an algal biomass or a supernatant having general health support and healthy immune system support properties may comprise obtaining a sample of the biological material of NCMA Deposit #PATENT201602001 and separating the solid and liquid components to obtain the algal biomass and supernatant respectively. In various embodiments, the biological material of NCMA Deposit #PATENT201602001 comprises at least one *klebsormidium* species of algae.

An algal biomass may be formulated into a composition or a supplement comprising the algal biomass, such as, for example, by suspending or milling the algal biomass in vegetable oil or other vehicle to form a paste, or by grinding into a powder along with various excipients for filling capsules or for compressing into tablets or caplets. These aspects are discussed in more detail below.

A supernatant may be obtained during the process of drying at least one algae species to produce an algal biomass. In various embodiments, a supernatant obtained from wet algae (e.g. by simply compressing the wet algae in a press or allowing the liquid to drain therefrom) general health support and healthy immune system support properties that may be identical, partly similar, or entirely different from the properties exhibited by the algal biomass. Each of these materials may then be separately processed and compounded as needed to produce finished products, such as tablets or injectable liquids, which can be administered to humans or non-human animals. Thus, in various aspects, drying of at least one species of algae produces two separate nutritionally useful materials, namely, a supernatant and an algal biomass. For example, a supernatant derived from the drying of at least one species of algae is concentrated down (e.g. by evaporative removal of water and other volatiles) to a syrup or other concentrate. A supernatant concentrated down to syrup may exhibit general health support and healthy immune system support properties. Syrup thus obtained may be diluted to a tonic or an injectable. In certain aspects, a supernatant and an algal biomass are both obtained from a *klebsormidium* species of algae by compressing the liquid from the *klebsormidium* species of algae to obtain the supernatant and, optionally, further desiccating the remaining solid plant material to produce the algal biomass. In various embodiments, the biological material of NCMA Deposit #PATENT201602001 comprises at least one *klebsormidium* species of algae and is useful for processing into both a supernatant and an algal biomass.

A supernatant can be produced by obtaining a sample of the biological material of NCMA Deposit #PATENT201602001 and draining off the liquid under gravity flow. The liquid thus obtained is termed the "supernatant." Furthermore, a sample of the biological material of NCMA Deposit #PATENT201602001 may be physically compressed to squeeze out supernatant from the cellular material. The solid matter left behind in either of these mechanical processes is an algal biomass in accordance to the present disclosure. In order to express the nutrients efficiently out from the intracellular space of intact cells, live or dead, algal cells may be chemically lysed or mechanically broken open to produce a more nutrient enriched supernatant upon separation of solid and liquid materials.

An algal biomass may be used as starting material for various extracts, derivatives, and homeopathic compounds therefrom that are directly useful for human or non-human animal health and nutrition, or that can be compounded into compositions or supplements useful for same. For example, an algal biomass can be manipulated, such as solvent extracted, to provide any number of extracts, derivatives and/or homeopathic compounds from the starting algal biomass. The solvent extracts from an algal biomass may be further manipulated, such as by high-pressure liquid chromatography (HPLC) or distillation to obtain individual homeopathic compounds or mixtures of homeopathic compounds. For example, an algal biomass may be solvent extracted and the combined extracts subjected to HPLC to isolate various natural products found in the living algal specie(s). In various embodiments, manipulation of an algal biomass may change the nature (e.g. the chemical structure) of one or more compounds present, such that one or more homeopathic compounds may be found and isolated that were not naturally present in the starting fresh/raw algae culture. For example, manipulation of an algal biomass may result in the isolation of compounds that are derivatives of substances naturally occurring in the starting algae (e.g. a salt of a naturally occurring carboxylic acid, a cyclic anhydride of a naturally occurring dicarboxylic acid, or a denatured protein of a naturally occurring protein in the algae, and so forth).

One or more of an extract, derivative, and homeopathic compound derived from an algal biomass that is further derived from at least one species of algae promotes or supports the general health and promotes or supports a healthy immune system in a human or non-human animal. In various aspects, one or more of an extract, derivative, and homeopathic compound is derived from an algal biomass that is further derived from a *klebsormidium* species of algae, wherein the one or more of an extract, derivative, and homeopathic compound promotes or supports the general health and promotes or supports a healthy immune system in an animal. Further, any of these substances derived from an algal biomass that is further derived from at least one species of algae may be further compounded into a composition or supplement usable for human nutritional support. In various embodiments, a sample of biological material of NCMA Deposit #PATENT201602001 provides an algal biomass further comprising at least one *klebsormidium* species of algae.

An algal biomass may be derived from the genus *Klebsormidium*. *Klebsormidium* is a genus of filamentous charophyte green algae of 20 known species, including *K. acidophilum, K. bilatum, K. crenulatum, K. dissectum, K. drouetii, K. elegans, K. flaccidum, K. fluitans, K. fragile, K. klebsii, K. lamellosum, K. montanum, K. mucosum, K. nitens, K. pseudostichococcus, K. scopulinum, K. sterile, K. subtile, K. subtilissimum,* and *K. tribonematoideum*. In various embodiments, an algal biomass is derived from any presently known, or yet to be discovered, species of *Klebsormidium* algae. In various embodiments, an algal biomass comprising at least one *Klebsormidium* species of algae is obtained by processing the biological material of NCMA Deposit #PATENT201602001.

For example, an algal biomass may be derived from an algae species selected from the group consisting of *K. acidophilum, K. bilatum, K. crenulatum, K. dissectum, K. drouetii, K. elegans, K. flaccidum, K. fluitans, K. fragile, K. klebsii, K. lamellosum, K. montanum, K. mucosum, K. nitens, K. pseudostichococcus, K. scopulinum, K. sterile, K. subtile, K. subtilissimum, K. tribonematoideum,* and mixtures thereof.

Furthermore, an algal biomass may be derived from algae species selected from the group consisting of *klebsormidium nitens, klebsormidium flaccidum,* and mixtures thereof. In various embodiments, an algal biomass may be derived from *klebsormidium nitens*. Also, an algal biomass may be derived from *klebsormidium flaccidum*.

An algal biomass may be used in its raw form as a nutritional health supplement for animals in general. Raw algal biomass may appear, for example, as a wet mass of cellular material, or may be further processed to another form that is more practical for non-human animals and in some instances more palatable, convenient or acceptable for humans. For example, an algal biomass can be processed to extract water-soluble or solvent-soluble contents, then those extracts concentrated and sterilized into a tonic supplement or an injectable or infusible liquid. In various other aspects, such as for livestock health maintenance, algal biomass in its raw form may be simply loaded into a syringe and distributed into the mouth of an animal as a food supplement, nutraceutical, or homeopathic, or the like. For human consumption, an algal biomass in its raw form may be mixed into blended fruit/vegetable drinks or added to soups or stews, or added to other foods as a food supplement. Or in other examples, liquid materials derived from at least one species of algae may be naturally or artificially colored and/or flavored, preserved or stabilized.

An algal biomass can be further processed to remove cellular cytoplasmic material and cell walls to leave behind what are primarily mixtures comprising algal flavonoids, phyto-hormones, fatty acids, polysaccharides, and the like. Different forms (e.g. raw or further processed as described, etc.) may be desired depending on the desired product form, route of administration, animal type (particularly whether human or non-human), prophylactic effect sought, amongst other considerations.

Nutritional Analysis:

A freeze-dried sample of the algal biomass obtained by processing the biological material of NCMA Deposit #PATENT201602001 (the process as described in detail herein above), was determined to contain a variety of nutrients important for human health. Furthermore, the freeze-dried algal biomass was virtually completely odorless and tasteless, and was free of heavy metals, harmful microbes, and toxins. TABLE 1 lists key nutritional components present in a freeze-dried sample of algal biomass (nutrient amounts refer to the amount of the nutrient present in 100 grams freeze-dried algal biomass). All of the nutritional analyses were performed at the National Food Laboratory. From these results, it can be seen the algal biomass is an ideal plant-based source of protein absent starchy carbohydrates.

TABLE 1

Key Nutrients Present in Freeze-Dried Algal Biomass

| NUTRIENT | AMOUNT PER 100 G ALGAL BIOMASS |
|---|---|
| Vitamin A | 24,425 IU |
| Vitamin C | 118 mg |
| Calcium | 79 mg |
| Protein | 43 grams |

TABLE 2 sets forth the complete nutritional analysis of the algal biomass, from which the key nutrients in TABLE 1 were selected for emphasis. In the table, "wt. %" refers to percentage on a weight/weight basis.

TABLE 2

Nutritional Analysis of the Algal Biomass

| Analyte | Value | Method Used |
|---|---|---|
| Cis-cis-Polyunsaturated Fat (wt. %) | 5.41 | AOAC 996.06 |
| Monounsaturated Fat (wt. %) | 0.13 | AOAC 996.06 |
| Saturated Fat (wt. %) | 2.15 | AOAC 996.06 |
| Total Fat (wt. %) | 8.04 | AOAC 996.06 |
| Trans Fat (wt. %) | 0.01 | AOAC 996.06 |
| Fructose (wt. %) | <0.25 | CM4200 |
| Glucose (wt. %) | 0.49 | CM4200 |
| Lactose (wt. %) | <0.25 | CM4200 |
| Maltose (wt. %) | <0.25 | CM4200 |
| Sucrose (wt. %) | <0.25 | CM4200 |
| Total Sugars (wt. %) | 0.49 | CM4200 |
| Ash (wt. %) | 3.80 | CM4001 |
| Calcium (mg/100 g) | 79.4 | CM5004 |
| Calories (Cal/10 g) | 411 | Calculation |
| Carbohydrates (wt. %) | 42.02 | Calculation |
| Cholesterol (mg/100 g) | <1 | (subcontracted) |
| Iron (mg/100 g) | 7.36 | CM5004 |
| Moisture (wt. %) | 3.54 | CM4012 |
| Protein (wt. %) | 42.6 | CM4006 |
| Sodium (mg/100g) | 172.2 | CM5004 |
| Total Dietary Fiber (wt. %) | 23.9 | AOAC 991.43 |
| Vitamin A (beta carotene) (IU/100 g) | 24,425 | MN4101 |
| Vitamin C (mg/100 g) | 117.98 | CM4104 |

TABLE 3 sets forth a comparative nutritional profile illustrating how the algal biomass in accordance to the present disclosure compares to other foods.

TABLE 3

Comparative Nutritional Profile

|  | Algal Biomass (100 g, dried) | Spirulina algae (100 g, dried) | beef liver (3 oz., raw) | spinach (1 cup, raw) | orange (medium-sized) | yogurt (1 cup, plain, whole milk) | Muscle Milk protein powder (100 g) | Soy beverage w/protein powder (100 g) |
|---|---|---|---|---|---|---|---|---|
| Vitamin A | 24,425 IU | 570 IU | 14,363 IU | 2813 IU | 295 IU | 243 IU | 2500 IU | 0 IU |
| Vitamin C | 118 mg | 10 mg | 1 mg | 8 mg | 70 mg | 1 mg | 30 mg | 0 mg |
| Calcium | 79 mg | 120 mg | 4 mg | 30 mg | 52 mg | 296 mg | 500 mg | 178 mg |
| Protein | 43 g | 57 g | 17 g | 0 g | 1 g | 9 g | 46 g | 56 g |
| Iron | 7 mg | 29 mg | 4 mg | 0 mg | 0 mg | 0 mg | 9 mg | 12 mg |
| Fiber | 24 g | 4 g | 0 g | 0 g | 3 g | 0 g | 7 g | 7 g |
| Sodium | 172 mg | 1048 mg | 59 mg | 24 mg | 0 mg | 113 mg | 329 mg | 733 mg |
| Cholesterol | 0 mg | 0 mg | 234 mg | 0 mg | 0 mg | 32 mg | 21 mg | 0 mg |

TABLE 4 sets forth a comparison of the protein content and amino acid content in the algal biomass to other food sources of protein. The presence of an asterisk (*) adjacent to an amino acid in the table indicates the amino acid is an essential amino acid.

TABLE 4

Comparative Protein Content

| Per 100 grams of product | Freeze dried algal biomass | BlueWave Fish Protein Isolate (CONC) | Advance Fish Protein Powder (CONC) | Source Organic Whey (CONC) | Soy flour, defatted (CONC) | Whey, acid, dried (Natural) | Spirulina, dried (Natural) |
|---|---|---|---|---|---|---|---|
| Protein in grams | 42.6 | 85 | 87 | 85 | 51.46 | 11.73 | 57.47 |
| Aspartic acid (g) | 2.22 | 1.68 | 1.33 | 2.50 | 2.87 | 2.45 | 2.52 |
| Alanine (g) | 1.88 | 1.32 | 0.85 | 0.94 | 1.08 | 1.09 | 1.97 |
| Arginine (g) | 1.67 | 1.35 | 0.87 | 0.31 | 1.77 | 0.70 | 1.81 |
| Cystine (g) | 0.23 | 0.00 | 0.24 | 0.08 | 0.37 | 0.45 | 0.29 |
| Glutamic acid (g) | 2.43 | 2.48 | 1.93 | 5.32 | 4.43 | 4.48 | 3.65 |
| Glycine (g) | 1.40 | 2.38 | 0.74 | 0.39 | 1.05 | 0.45 | 1.35 |
| Histidine (g)* | 0.38 | 0.25 | 0.36 | 0.23 | 0.62 | 0.49 | 0.47 |
| Isoleucine (g)* | 0.94 | 0.63 | 0.59 | 1.17 | 1.11 | 1.24 | 1.40 |
| Leucine (g)* | 1.98 | 1.19 | 1.02 | 2.42 | 1.86 | 2.39 | 2.15 |
| Lysine (g)* | 1.21 | 1.10 | 1.14 | 1.95 | 1.52 | 2.15 | 1.31 |

TABLE 4-continued

Comparative Protein Content

| Per 100 grams of product | Freeze dried algal biomass | BlueWave Fish Protein Isolate (CONC) | Advance Fish Protein Powder (CONC) | Source Organic Whey (CONC) | Soy flour, defatted (CONC) | Whey, acid, dried (Natural) | Spirulina, dried (Natural) |
|---|---|---|---|---|---|---|---|
| Methionine (g)* | 0.32 | 0.53 | 0.73 | 0.50 | 0.31 | 0.47 | 0.50 |
| Phenylalanine* | 1.34 | 0.66 | 0.54 | 0.47 | 1.19 | 0.83 | 1.21 |
| Proline (g) | 1.20 | 1.20 | 0.55 | 1.48 | 1.34 | 1.49 | 1.04 |
| Serine (g) | 1.02 | 1.15 | 0.48 | 1.09 | 1.32 | 1.15 | 1.31 |
| Threonine (g)* | 1.17 | 0.85 | 0.63 | 1.71 | 0.99 | 1.26 | 1.29 |
| Tryptophan (g)* | 0.51 | 0.00 | 0.31 | 0.23 | 0.33 | 0.51 | 0.40 |
| Tyrosine (g) | 0.90 | 0.54 | 0.45 | 0.47 | 0.86 | 0.64 | 1.12 |
| Valine (g)* | 1.25 | 0.82 | 0.67 | 1.03 | 1.14 | 1.24 | 1.53 |

TABLE 5 sets forth a comparison of selected nutrients in the algal biomass to other food sources, including both terrestrial food sources and another algae, *Spirulina*.

TABLE 5

Comparative Nutrient Content

| | Algal Biomass (100 g, dried) | Spirulina algae (100 g, dried) | beef liver (3 oz, raw) | spinach (1 cup, raw) | orange (medium-sized) | yogurt (1 cup, plain, whole milk) | Muscle Milk protein powder (100 g) | Soy beverage w/protein powder (100 g) |
|---|---|---|---|---|---|---|---|---|
| Vitamin A | 24,425 IU | 570 IU | 14,363 IU | 2813 IU | 295 IU | 243 IU | 2500 IU | 0 IU |
| Vitamin C | 118 mg | 10 mg | 1 mg | 8 mg | 70 mg | 1 mg | 30 mg | 0 mg |
| Calcium | 79 mg | 120 mg | 4 mg | 30 mg | 52 mg | 296 mg | 500 mg | 178 mg |
| Protein | 43 g | 57 g | 17 g | 0 g | 1 g | 9 g | 46 g | 56 g |
| Iron | 7 mg | 29 mg | 4 mg | 0 mg | 0 mg | 0 mg | 9 mg | 12 mg |
| Fiber | 24 g | 4 g | 0 g | 0 g | 3 g | 0 g | 7 g | 7 g |
| Sodium | 172 mg | 1048 mg | 59 mg | 24 mg | 0 mg | 113 mg | 329 mg | 733 mg |
| Cholesterol | 0 mg | 0 mg | 234 mg | 0 mg | 0 mg | 32 mg | 21 mg | 0 mg |

As shown in the nutritional analyses set forth above, the algal biomass obtained by processing the biological material of NCMA Deposit #PATENT201602001 provides a unique blend of protein, micronutrients, and non-starch polysaccharides.

Compounding Algal-Derived Materials into Compositions and Supplements for Human and Non-Human Animal Health and Nutrition The algal biomass or supernatant, or any extract, derivative or homeopathic compound derived therefrom, may be compounded into a supplement for human consumption. Physical forms of a supplement include, but are not limited to, pill, tablet, effervescent tablet, caplet, soft-gel capsule, hard powder filled capsule, chewable (wafer, nodule or any other shape), dissolving film (i.e. oral drug strip), liquid, syrup, cream, ointment, or tonic. These and other physical forms may be obtained by compounding at least one of an algal biomass or supernatant derived from at least one algal species, or by compounding extracts, derivatives, or homeopathic compounds derived therefrom, with any acceptable number and amount of excipients appropriate for the particular physical form. Appropriate excipients are well-known in the pharmaceutical arts and in vitamin compounding in general, and are listed in various handbooks, such as for example, Rowe, et al., eds., Handbook of Pharmaceutical Excipients, 7th Ed, London, Pharmaceutical Press, 2012. For example, an algal biomass or supernatant, or any extract, derivative or homeopathic compound therefrom, may be compounded into a supplement for human consumption with any number, type and quantity of excipients (e.g. water, solvent, oils, emulsifiers, dispersants, fillers, disintegrants, coatings, buffers, thickeners, gellants, surfactants, chelants, emollients, stabilizers, isotonic agents, preservatives, sweeteners, colorants, flavoring agents, etc.) to produce a desired and usable finished physical form for the supplement.

In a non-limiting example, a tablet, such as one resembling a retail consumer multivitamin, such as CENTRUM® (registered trademark of Pfizer), or a chewable multivitamin or soft chewable (often referred to as "gummy vitamins", or simply "gummies"), may comprise a mixture of ground or powdered freeze-dried algal biomass along with various amounts of binders, coatings, disintegrants, texturizing agents, gelling agents, colors, flavors, preservatives, and so forth. For example, a precursor dry powder blend for tableting may be optimized for a rotary tablet press, and may also be formulated and compressed at the appropriate conditions in order to exhibit a targeted disintegration rate when ingested. In other non-limiting examples, a soft chewable gummy vitamin may comprise a mixture of ground or powdered freeze-dried algal biomass compounded with sugars, syrup, water, gelatin, carnauba wax, coloring, flavors, and the like.

In non-limiting examples, a supplement for human consumption comprises from about 0.1 wt. % to 100 wt. % of an algal biomass derived from at least one species of algae. For example, to produce 100% algal biomass supplements in tablet form, (i.e. tableted supplements without any excipients therein), freeze dried (powdered or ground) algal biomass may be compressed in a rotary tablet press to produce 100% algal supplements. These supplements will have the nutritional analyses delineated in the tables above since there are no excipients present to "dilute" the nutrients present. In other embodiments, the amount of any nutrient present in a supplement that comprises less than 100 wt. % algal biomass may be calculated by multiplying the percentage of algal biomass present in the supplement with the amount of nutrient shown in the tables above. For example, a tableted supplement comprising 10% algal biomass and 90% total excipients will comprise about 2,442.5 IU Vitamin A.

In non-limiting examples, supplements for human consumption may comprise: 0.10 wt. % algal biomass/99.9 wt. % total excipients; 0.50 wt. % algal biomass/99.5 wt. % total excipients; 1.0 wt. % algal biomass/99.0 wt. % total excipients; 10 wt. % algal biomass/90 wt. % total excipients; 20 wt. % algal biomass/80 wt. % total excipients; 30 wt. % algal biomass/70 wt. % total excipients; 40 wt. % algal biomass/60 wt. % total excipients; 50 wt. % algal biomass/50 wt. % total excipients; 60 wt. % algal biomass/40 wt. % total excipients; 70 wt. % algal biomass/30 wt. % total excipients; 80 wt. % algal biomass/20 wt. % total excipients; 90 wt. % algal biomass/10 wt. % total excipients; 99.5 wt. % algal biomass/0.5 wt. % total excipients; 99.9 wt. % algal biomass/0.1 wt. % total excipients; or 100 wt. % algal biomass/0 wt. % total excipients.

The weight of a nutritional supplement in accordance with the present disclosure may be that of a typical retail hard vitamin tablet, chewable, or soft chewable supplement, such as for example, from about 0.25 grams per piece to about 10 grams per piece. For each supplement, the amount of any nutrient delivered may be calculated by multiplying the percentage of nutrient present by the weight of the supplement. For example, a 1 gram (1,000 mg) tableted supplement comprising 10 wt. % algal biomass will deliver (1.18 mg Vitamin C/1 gram algal biomass×10 wt. % algal biomass per tablet=0.118 mg Vitamin C per 1,000 mg supplement).

Liquid supplements for human nutritional support may comprise from about 0.1 wt. % to 100% supernatant or concentrated supernatant derived from at least one algal species. At the extreme end of the range, (100% supernatant or concentrated syrup therefrom in a liquid supplement), supernatant or concentrated syrup derived from at least one species of algae as described above may be provided "as is" (or "neat") to the human in need of nutritional support. In other examples, the supernatant or concentrated syrup therefrom, may be diluted with any amount of water or solvent as desired, and optionally made more palatable with any amounts of flavorings and/or colorings.

In non-limiting examples, liquid supplements for human consumption may comprise: 0.10 wt. % algal supernatant/99.9 wt. % total diluents; 0.50 wt. % algal supernatant/99.5 wt. % total diluents; 1.0 wt. % algal supernatant/99.0 wt. % total diluents; 10 wt. % algal supernatant/90 wt. % total diluents; 20 wt. % algal supernatant/80 wt. % total diluents; 30 wt. % algal supernatant/70 wt. % total diluents; 40 wt. % algal supernatant/60 wt. % total diluents; 50 wt. % algal supernatant/50 wt. % total diluents; 60 wt. % algal supernatant/40 wt. % total diluents; 70 wt. % algal supernatant/30 wt. % total diluents; 80 wt. % algal supernatant/20 wt. % total diluents; 90 wt. % algal supernatant/10 wt. % total diluents; 99.5 wt. % algal supernatant/0.5 wt. % total diluents; 99.9 wt. % algal supernatant/0.1 wt. % total diluents; or 100 wt. % algal supernatant/0 wt. % total diluents.

Solid-form and liquid-form supplements in accordance to the present disclosure may be packaged in any form of packaging suitable for retail or professional dispensation. Packaging examples include, but are not limited to, jars, bottles, and foil, plastic film or paper envelopes.

For non-human animals, such as for example, non-domesticated animals or livestock and other domestic farm animals, suitable product forms may relate to the nature of the algal material to be administered (e.g. dried algal biomass, supernatant from algae, etc.), route of administration, the type of animal in need of health maintenance, and the treatment regimen, amongst other considerations, and include, but are not limited to, loose powders and granulates, pellets, pills, tablets, capsules, drops, sprays, ointments, pastes, emulsions (W/O, O/W), suspensions, creams, foams, pomades, injectable liquids, infusible liquids, patches, suppositories, devices and implants.

In various embodiments, a liquid algal derived material, (e.g. a concentrated supernatant in syrup form, having been derived from compressing algae plant material to produce a supernatant and evaporation of volatiles from the supernatant to produce syrup) may be diluted in a sterile saline buffer or other sterile diluent to produce an injectable liquid or a liquid suitable for infusion, such as mammary infusion.

In various embodiments, a dry algal biomass, (e.g. after the freeze-drying or oven drying of algal plant material), may be packed into a capsule shell, ground to a powder, placed into the mouth of an animal directly, added to livestock feed, or compounded with a vehicle to produce an oral paste, or a transdermal, rectal or vaginal paste, emulsion or cream. In various embodiments, an algal biomass, a supernatant, an extract, a derivative, or a biologically active compound derived from any of the previous, may be further compounded into a pharmaceutical composition having any number, type and quantity of excipients (e.g. water, solvent, emulsifiers, dispersants, fillers, disintegrants, buffers, thickeners, surfactants, emollients, stabilizers, preservatives, colorants, flavors, etc.) to produce a desired and usable final dosage form. In various embodiments, the dosage form is a sterile injectable or infusible liquid, or a paste, or a wet suspension that can be loaded into the mouth of an animal.

A desired fluidity for the material being administered in accordance to the present disclosure can be targeted and maintained, for example, by the use of a diluent, emulsifier or suspending agent, e.g. for example water or lecithin, or by the use of a particular particle size in the case of dispersions, or by the use of surfactants or other additives. Non-aqueous vehicles such a cottonseed oil, sesame oil, olive oil, soybean oil, corn oil, sunflower oil, or peanut oil, and various esters, such as isopropyl myristate, may also be used as solvent systems for the compositions herein. Additionally, various additives which enhance the stability, sterility, and isotonicity of the compositions, including antimicrobial preservatives, antioxidants, chelating agents, and buffers, can be added. Various antibacterial and antifungal agents include, for example, parabens, chlorobutanol, phenol, sorbic acid, and the like. In various embodiments, compositions in accordance to the present disclosure further comprise isotonic agents, for example, sugars, sodium chloride, and the like. In various embodiments, a prolonged absorption of a product form can be brought about by the use of agents delaying absorption, for example, aluminum stearate and gelatin.

Methods of Prophylactic Treatment of Humans and Non-Human Animals:

As used herein, the term "prophylactically effective amount" in the context of administering an algal biomass, a supernatant, or compositions thereof, to an animal in need thereof, and in the context of administering at least one of an extract, derivative and homeopathic compound derived from an algal species or algal biomass, or compositions thereof, to a human or non-human animal in need thereof, refers to a sufficient amount of the administered material to provide a desired prophylactic effect, and takes into account such things as dose, product form, route of administration, animal type, general health assessment, manifestation of various ailments, and dosage regimen, amongst other considerations. A prophylactic effect can manifest as maintaining a healthy condition for an animal, e.g. general health, healthy immune system support, and prevention, reduction or delay in recurrence of particular diseases, the prevention, reduction or delay in the effects of stress, or an alleviation or delay of the effects of daily stress or event-related stress. In various embodiments, a prophylactically effective amount is that amount which keeps a person, a non-human animal or herd of animals in a healthier condition compared to persons or non-human animals not receiving an algal derived supplement. Thus, in some instances, a prophylactic effect may be seen as nothing happening to a person or a non-human animal, i.e. a healthy life with no disease or ailments.

For example, a "prophylactically effective amount" of algal-derived supernatant, or a liquid supplement obtained therefrom, for promoting a person's general health, for promoting a person's healthy immune system, or for supporting or promoting general health or healthy immune system in an non-human animal, may be from about 0.001 mL to about 100 mL per day, such as ingested daily, with or without a meal, or administered by injection or infusion throughout the life of the person or animal. In another non-limiting example, a "prophylactically effective amount" of algal biomass for promoting a healthy immune system in a human or non-human animal may be from 0.5 ounces to about 5 ounces fed to the person or animal every day for life.

In various embodiments pertaining to human health, a "prophylactically effective amount" of a supplement in tablet form, such as for promoting a person's general health or for promoting a person's healthy immune system, may be from about 1 to about 8 tablets per day (each weighing from about 0.25 grams to about 2 grams), taken with or without a meal. Liquid or tablet supplements may be taken with other vitamins, such as a standard commercial multivitamin, each day for as long as a person feels necessary, which may be for a person's entire lifetime. A supplement for human nutritional health and support, comprising an algal biomass or supernatant derived from at least one algal species, or comprising any one of an extract, derivative, and homeopathic compound derived from at least one species of algae, may be administered to the person in need of health maintenance via any route of administration, in any suitable dosage form, and in accordance to any supplement regimen. In various embodiments, a supplement regimen may follow a daily schedule in combination with a multivitamin or other vitamin supplements.

In accordance to the present disclosure, the methods of promoting general health and promoting a healthy immune system in an animal in accordance with the present disclosure are applicable to any animal in need of health maintenance. Examples of animals suitable as subjects for prophylactic treatment according to the present methods include, but are not limited to, bovine animals (e.g. beef and dairy cattle), ovine animals, caprine animals, camelids, equidae, goats and other ruminant animals, porcine animals, and other livestock animal commercial or otherwise, canine animals including domestic dogs, feline animals including domestic cats, ursine animals, primates, mammals in general, and humans.

An algal biomass or supernatant derived from at least one algal species, or any one of an extract, derivative and biologically active compound derived from at least one species of algae or from an algal biomass, or compositions comprising any of the foregoing, may be administered to a non-human animal in need of health maintenance via any route of administration, in any suitable dosage form, and in accordance to any treatment regimen.

For example in human health maintenance, suitable supplement regimens include, but are not limited to, a single dosage (e.g. a one-time supplement pill or tablet), more than one dose, at least one dosage per day for more than a day, daily dosages as nutritional supplements for the entire life of the person, daily addition to various meals for the life of the person, and the like. Nutritional supplement regimens may commence at the first evidence or knowledge of everyday or event-related stress, or any observable unhealthiness in the person (e.g. low weight, fatigue, depression, etc.), or at any other time for any prophylactic treatment. In various embodiments, doses can be single doses or multiple doses over a period of several days, months, years, or entire lifetime of the person.

For health maintenance in other animals besides humans, such as farm animals, suitable treatment regimens include, but are not limited to, a single dosage (e.g. a one-time pill or injection), more than one dose, at least one dosage per day for more than a day, daily dosages as supplements for the life of the animal, daily addition to animal feed for the life of the animal, and the like. As per humans, treatment regimens may commence at the first evidence or knowledge of stress or any observable unhealthiness in an animal (e.g. low weight), or at any other time for any prophylactic treatment. In various embodiments, doses can be single doses or multiple doses over a period of several days, months, years, or lifetime of the animal. For administering algal supplements of the present disclosure parenterally, they can generally be formulated in a unit dosage injectable form (solution, suspension, emulsion). The prophylactic formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

A majority of the practical routes of administration apply to both humans and other animals. Routes of administration include, but are not limited to, oral, sublingual, buccal, nasal, intrasinal, mucosal, ophthalmic, conjunctival, parenteral, intravenous, intramuscular, intralymphatic, intraductal, rectal, vaginal, topical, and transmammary (e.g. intramammary infusion). In various embodiments, a route of administration is chosen from the group consisting of orally, subcutaneously, parenterally including intravenous, intraarterial, intramuscular, intraperitoneally, intratonsillar, intranasal, intramammary, intrathecal and infusion. For example, an algal biomass, supernatant, extract, derivative, or prophylactic compound from at least one algae species may be administered parenterally to an animal in a slow-release form.

In various embodiments, administration of an algal biomass, supernatant, extract, derivative or homeopathic compound derived therefrom, can be orally, especially in the processed form. Alternatively, administration can be topically and the aseptic extracts or isolates of the algal biomass can be applied directly to the skin of an animal. Other product forms can include, for example, oral (e.g. with further processing to remove cellular material) or parenteral (e.g. with any necessary sterilization).

A supplement comprising an algal biomass or supernatant derived from at least one species of algae, or an extract, derivative or biological compound obtained therefrom, may be used to promote general health in humans, promote a person's healthy immune system, and/or prevent, reduce or delay the recurrence of any human disease or any effects of everyday or event-related stress in an human. Diseases that may recur in unhealthy persons include, but are not limited to, acne vulgaris, asthma, autoimmune diseases, celiac disease, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, interstitial cystitis, atherosclerosis, allergies, myopathies, leukocyte defects, cancer, endometriosis, and multiple sclerosis. Unhealthy physical conditions may also manifest as low body weight for the age of the person, sluggishness, fatigue, multiple chemical sensitivities, asthma, difficulties breathing, mental depression, and the like.

An algal biomass or a supernatant derived from at least one species of algae, or an extract, derivative or prophylactic compound obtained therefrom, is used to promote general health in an animal, promote an animal's healthy immune system, and/or prevent, reduce or delay the recurrence of any disease or any effects of stress in an animal. Diseases that may recur in unhealthy or stressed animals include, but are not limited to, acne vulgaris, asthma, autoimmune diseases, celiac disease, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, interstitial cystitis, atherosclerosis, allergies, myopathies, leukocyte defects, cancer, endometriosis, bovine mastitis, Bovine Respiratory Disease Complex, and multiple sclerosis. Unhealthy states and stress in an animal may also manifest as low weight for the age of the animal, sluggishness, poor milk or egg production, and the like.

In various embodiments, a method of preventing, reducing, or delaying recurrence of a disease in a human or animal, reducing stress in an animal, preventing, reducing, or delaying the effects of stress in an animal, reducing daily life stress or event-related stress, preventing, reducing, or delaying the effects of daily life stress or event-related stress in a human, maintaining general health in a human or animal, or maintaining a healthy immune system in a human or animal, comprises administering to the human or non-human animal in need thereof a prophylactically effective amount of an algal biomass or supernatant derived from at least one species of *klebsormidium*. In various embodiments, the at least one species of algae is selected from the group consisting of *klebsormidium nitens, klebsormidium flaccidum*, and mixtures thereof. The at least one species of algae may comprise *klebsormidium nitens*. Further, the at least one species of algae may comprise *klebsormidium flaccidum*. In certain aspects, an algal biomass or supernatant is obtained by processing the biological material of NCMA Deposit #PATENT201602001, wherein the biological material comprises at least one species of *klebsormidium*.

In various embodiments, the condition or disease thus prevented, reduced or delayed from recurring is chosen from the group consisting of acne vulgaris, asthma, autoimmune diseases, celiac disease, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, interstitial cystitis, atherosclerosis, allergies, myopathies, leukocyte defects, cancer, endometriosis, multiple sclerosis, stress, anxiety, chronic depression, and combinations thereof.

Methods of Maintaining General Health and/or for Maintaining a Healthy Immune System in a Human or Non-Human Animal:

A method of maintaining general health and a healthy immune system in a human or non-human animal comprises administering to the animal in need thereof a prophylactically effective amount of an algal biomass derived from at least one species of algae. In various embodiments, a method of maintaining general health and a healthy immune system in an animal comprises administering to the animal in need thereof a prophylactically effective amount of a composition comprising an algal biomass derived from at least one species of algae. In various embodiments, a method of maintaining general health and a healthy immune system in an animal comprises administering to the animal in need thereof a prophylactically effective amount of a supernatant obtained from drying at least one species of algae. In various embodiments, a method of maintaining general health and a healthy immune system in an animal comprises administering to the animal in need thereof a prophylactically effective amount of at least one of an extract, derivative and homeopathic compound derived from an algal biomass further derived from at least one species of algae. In various embodiments, the at least one species of algae comprises a *klebsormidium* species of algae. In various embodiments, the at least one species of algae is selected from the group consisting of *klebsormidium nitens, klebsormidium flaccidum*, and mixtures thereof. In various embodiments, the at least one species of algae comprises *klebsormidium nitens*. In various embodiments, the at least one species of algae comprises *klebsormidium flaccidum*. An algal biomass or supernatant may be obtained by processing the biological material of NCMA Deposit #PATENT201602001, wherein the biological material comprises at least one species of *klebsormidium*.

A method of maintaining general health and a healthy immune system in a human or non-human animal comprises administering to the animal in need thereof a prophylactically effective amount of an algal biomass derived from at least one *klebsormidium* algae species. In various embodiments, the at least one *klebsormidium* algae species comprises *klebsormidium nitens*. An algal biomass may be obtained by processing the biological material of NCMA Deposit #PATENT201602001, wherein the biological material comprises at least one species of *klebsormidium*.

A method of maintaining general health and a healthy immune system in a human or non-human animal comprises administering to the animal in need thereof a prophylactically effective amount of a concentrated extract of an algal biomass derived from at least one *klebsormidium* algae species. In various embodiments, the at least one *klebsormidium* algae species comprises *klebsormidium nitens*. An algal biomass may be obtained by processing the biological material of NCMA Deposit #PATENT201602001, wherein the biological material comprises at least one species of *klebsormidium*.

A method of maintaining general health and a healthy immune system in a human or non-human animal comprises administering to the animal in need thereof a prophylactically effective amount of a supernatant obtained from the drying of at least one *klebsormidium* algae species. In various embodiments, the at least one *klebsormidium* algae species comprises *klebsormidium nitens*. A supernatant may be obtained by processing the biological material of NCMA Deposit #PATENT201602001, wherein the biological material comprises at least one species of *klebsormidium*.

A method of maintaining general health and a healthy immune system in a human or non-human animal comprises administering to the animal in need thereof a prophylactically effective amount of at least one of an extract, derivative and homeopathic compound derived from an algal biomass further derived from at least one *klebsormidium* algae species. In various embodiments, the at least one *klebsormidium* algae species comprises *klebsormidium nitens*. An algal biomass may be obtained by processing the biological material of NCMA Deposit #PATENT201602001, wherein the biological material comprises at least one species of *klebsormidium*.

Methods of Preventing, Reducing or Delaying the Onset or Recurrence of an Effect of Stress in a Human or Non-Human Animal:

A method of preventing, reducing or delaying the onset or recurrence of an effect of stress in a human or non-human animal comprises administering to the animal in need thereof a prophylactically effective amount of an algal biomass derived from at least one species of algae. In various embodiments, a method of preventing, reducing or delaying the onset or recurrence of an effect of stress in an animal comprises administering to the animal in need thereof a prophylactically effective amount of a composition or a supplement comprising an algal biomass derived from at least one species of algae. In various embodiments, a method of preventing, reducing or delaying the onset or recurrence of an effect of stress in an animal comprises administering to the animal in need thereof a prophylactically effective amount of a supernatant obtained, for example, from drying at least one species of algae. In various embodiments, a method of preventing, reducing or delaying the onset or recurrence of an effect of stress in an animal comprises administering to the animal in need thereof a prophylactically effective amount of at least one of an extract, derivative and homeopathic compound derived from an algal biomass further derived from at least one species of algae. In various embodiments, the at least one species of algae comprises a *klebsormidium* species of algae. In various embodiments, the at least one species of algae is selected from the group consisting of *klebsormidium nitens*, *klebsormidium flaccidum*, and mixtures thereof. For example, the at least one species of algae comprises *klebsormidium nitens*. In other aspects, the at least one species of algae comprises *klebsormidium flaccidum*. An algal biomass or supernatant may be obtained by processing the biological material of NCMA Deposit #PATENT201602001, wherein the biological material comprises at least one species of *klebsormidium*. In humans, stress may be everyday stress, physical or mental, or event-related stress, such as caused by at least one traumatic emotional event.

EXAMPLES

Example 1

Preparation of an Algal Biomass (Single Culture to Small Culture)

A sample of NCMA Deposit #PATENT201602001 was used to grow algae axenically on an mBBM agar petri plate. The sample comprises at least one *klebsormidium* algae species. A single colony was picked from the plate and grown in mBBM media in a shake flask for one month to achieve adequate density for roux bottle inoculation. Algae inoculum grown in roux bottles was progressively divided to produce the minimum inoculation density required for panel reactor growth. Algae biomass grown in reactors was placed in a 25 μm filter sock to remove supernatant using gravity flow. Excess supernatant was removed with manual squeezing of the filter sock until the consistency of the algal biomass reached a thick paste. The algal biomass was then spread into a ½ inch layer on a stainless steel tray and placed at −80° C. until frozen. The tray was then moved to a vacuum equipped freeze-drier, and the material held at −50° C. to −60° C. for several days until the moisture level was reduced to about 5 to 10% by weight. The freeze-dried algal biomass was stored in a refrigerator at 4° C. or in a freezer at −20° C. until use.

Example 2

Preparation of an Algal Biomass (Scale-Up of Small Culture)

Monocultures of a filamentous alga are grown in 120 L and 240 L flat panels with a 4-inch light path, 3-9 mM $NO_3$ in mBBM media, and $CO_2$/air mixing or within outdoor, covered, HEPA filtered ponds using natural light. Harvesting consist of drawing off the liquid and algae that is contained in the liquid and separating the liquid from the algal biomass. There is typically about 1.4 grams of algae per liter of water. Upon harvesting, biomass is placed in a 25 μm filter sock to remove water using gravity flow. Excess water is removed with manual squeezing resulting in a wet paste that is about 15% solids and 85% water. The appearance of the biomass is that of a bright green thick paste. On average, about 8-10 kg wet weight yields about 1 kg of algal biomass in the form of a paste. This material is then spread onto stainless steel trays in a ½" layer and placed in a −80° C. freezer until frozen or ready for further processing. Freeze dried biomass is achieved by placing the tray in a freeze-drier equipped with a vacuum pump and set at −50° C. to −60° C. for several days until the moisture level was reduced to 5-10%. Freeze-dried biomass was stored in a refrigerator at 4° C. or freezer at −20° C. until use. The freeze dried algal biomass material produced in accordance to this method effectively has no water and is in the form of a dark green powder or a brittle cake.

Example 3

Maintenance of General Health and a Healthy Immune System in Beef and Dairy Cattle The algal biomass prepared in accordance to Example 2 was removed from cold storage immediately prior to use. 3 oz. of algal biomass was suspended in a small amount of distilled water such that it could be administrable to an animal orally. This unrefined and minimally processed algal biomass can be administered orally to individuals in a group of animals or to animals in an entire herd once a day via an administration gun equipped with a syringe, loaded with 3 oz. of the suspended algal biomass for each dosage, over the lifetime of each animal. It is contemplated that oral administration of suspended algal biomass assists in maintenance of general health in an animal and the promotion of a healthy immune system in an animal.

Example 4

Maintenance of General Health and a Healthy Immune System in Humans

The algal biomass prepared in accordance to Example 2 was removed from cold storage immediately prior to use. From about 0.001 oz. to about 3 oz. of algal biomass may be added directly to various foods for human consumption as a method of supplementing human nutrition. This unrefined and minimally processed algal biomass can be suspended in water and administered orally to individuals or added to foods such as vegetable purees. In other variations, the freeze dried algal biomass as detailed above may be compounded with various excipients and then processed into a supplement, such as a tablet. In non-limiting examples, from about 1 to about 8 tablets may be consumed per day by the person in need of nutritional support.

Example 5

Preparation of a Supernatant

Monocultures of a filamentous alga are grown in 120 L and 240 L flat panels with a 4-inch light path, 3-9 mM $NO_3$ in mBBM media, and $CO_2$/air mixing or within outdoor, covered, HEPA filtered ponds using natural light. Harvesting consist of drawing off the liquid and algae that is contained in the liquid and separating the liquid from the algal biomass. There is typically about 1.4 grams of algae per liter of water. Upon harvesting, supernatant is collected as the harvest is passed through a 25 μm filter sock until it is clear of algae. The clarified supernatant is transferred to previously-sanitized 60 gal barrels and stored at 4° C. until filtration and concentration. The appearance of the clarified supernatant is that of a clear liquid (i.e., water). Supernatant is processed through a filtration unit which passes the liquid through 0.5 μm (×4) 0.45 μm (×1) and 0.2 μm (×1) filters in series to remove any contaminating matter. Supernatant is concentrated anywhere from 10 to 500 times using a rotary evaporator. The appearance of concentrated supernatant varies with degree of concentration, from a clear liquid having the consistency of regular tap water, to a yellow, viscous, syrup-like liquid in higher concentrations.

Example 6

Maintenance of General Health and a Healthy Immune System in a Human or Non-Human Animal The supernatant prepared in Example 5, having syrup-like consistency after concentration, was diluted with sterile water to produce an injectable liquid. The injectable liquid can be administered by intramammary intubation, subcutaneous injection, or intramuscular injection, or the like, to each animal every day or more for several days, weeks, months, years or the lifetime of the animal. For example, to maintain health, animals can be administered 20 mL 100× supernatant, or 30 mL 100× supernatant once a day for the life of the animal. For human health, the supernatant prepared in Example 5, diluted or concentrated as needed, may be consumed as a liquid supplement by the person in need of nutritional support at a dosage of from about 0.001 mL to about 100 mL one or more times per day. The liquid supplement may be consumed by the person in need thereof every day or more for several days, weeks, months, years or for the person's entire lifetime.

It will be apparent to those skilled in the art that various modifications and variations can be made to the present disclosure without departing from the spirit or scope of the disclosure. Thus, it is intended that the present disclosure cover the modifications and variations of this disclosure provided they come within the scope of the appended claims and their equivalents.

We claim:

1. A method of human or non-human animal care, said method comprising administering to the human or non-human animal in need thereof, a prophylactically effective amount of a supplement comprising an algal species of *Klebsormidium* of NCMA Deposit # PATENT20160200, wherein said care comprises reduction or prevention of an effect of stress.

2. The method of claim 1, wherein said effect of stress is selected from the group consisting of dehydration, loss of energy, an imbalance of symbiotic bacteria, low body weight, fatigue, chronic depression, low milk production, low egg production, gastrointestinal disorders, and combinations thereof.

* * * * *